United States Patent [19]
Stenger et al.

[11] Patent Number: 6,103,534
[45] Date of Patent: Aug. 15, 2000

[54] CYCLONE AEROSOL SAMPLER AND BIOLOGICAL AEROSOL CHEMILUMINESCENT DETECTION SYSTEM EMPLOYING THE SAME

[75] Inventors: David A. Stenger, Herndon, Va.; James P. Whelan, Chicago, Ill.

[73] Assignee: The United States of America as represented by the Secretary of the Navy, Washington, D.C.

[21] Appl. No.: 09/407,372

[22] Filed: Sep. 28, 1999

[51] Int. Cl.$^7$ .................................................. G01N 21/76
[52] U.S. Cl. ........................... 436/63; 436/172; 436/181; 422/52; 435/30; 73/28.01
[58] Field of Search ................................ 422/52; 436/63, 436/52, 172, 181; 435/30, 8; 73/28.01, 31.07; 250/361 C

[56] References Cited

U.S. PATENT DOCUMENTS

| | | |
|---|---|---|
| 3,567,586 | 3/1971 | Soli . |
| 3,690,837 | 9/1972 | Witz et al. .............................. 23/254 R |
| 3,754,868 | 8/1973 | Witz et al. .............................. 23/254 R |
| 3,797,999 | 3/1974 | Witz et al. .............................. 23/230 R |
| 3,940,250 | 2/1976 | Plakas et al. . |
| 3,959,081 | 5/1976 | Witz et al. ......................... 195/103.5 R |
| 3,984,688 | 10/1976 | Von Bargen et al. ................... 250/361 |
| 4,176,007 | 11/1979 | Jeffers et al. ............................... 435/34 |
| 4,385,113 | 5/1983 | Chappelle et al. ........................... 435/8 |
| 4,755,055 | 7/1988 | Johnson et al. .......................... 356/440 |
| 4,765,961 | 8/1988 | Schiff et al. ............................... 422/52 |
| 5,445,794 | 8/1995 | Wihlborg ................................... 422/63 |
| 5,773,710 | 6/1998 | Squirrell ................................. 73/28.01 |
| 5,918,259 | 6/1999 | Squirrell ................................. 73/28.01 |

OTHER PUBLICATIONS

Upton et al., "A Wind Tunnel Evaluation of the Physical Sampling Efficiencies of Three Bioaerosol Samplers," J. Aerosol Sci., vol. 25, No. 8, pp. 1493–1501 (1994).

Ewetz et al., "Factors Affecting the Specificity of the Luminol Reaction with Hematin Compounds," Anal. Biochem. 71:564–70 (1976).

Hecker, "Technology Assessment of Holy Grail," Draft Final Report by Battelle to National Ground Intelligence Center, Contract No. DAHC90–95–D–0006 (Sep. 1997).

Thorpe et al., "Enhanced Chemiluminescent Reactions Catalyzed by Horseradish Peroxidase," Meth. Enzymol., 133:331–54, (1986).

Primary Examiner—Jeffrey Snay
Attorney, Agent, or Firm—Barry A. Edelberg; John J. Karasek

[57] ABSTRACT

An improved biological aerosol chemiluminescent (CL) detection system having optimal sensitivity and a method for using the same in detecting the presence of biological materials in an aerosol sample. The detection system comprises a cyclone aerosol sampler, a CL reagent injector, and a luminometer, wherein the CL reagent injector is mated with the cyclone aerosol sampler so as to deliver/introduce CL reagent thereto. The inner surface of the cyclone aerosol sampler and the inner surface of the CL reagent injector are fabricated from materials that are free of metals that would initiate a CL-based reaction with a CL reagent to be employed therein so as to provide a CL reagent path free of these metals. The entire CL reagent path in the biological aerosol CL detection apparatus is comprised of these materials. A method for determining the suitability of materials for use throughout the CL reagent path of the biological CL detection system is also taught.

32 Claims, 6 Drawing Sheets

**MANUAL CHEMILUMINESCENT SYSTEM TEST -
Bg AEROSOL - KYNAR SAMPLER, 1' SAMPLE CYCLE**

(Background compared to challenges
of 75,000 total particles of Bacillus globigii)

*FIG. 6*

CYCLONE AEROSOL SAMPLER AND BIOLOGICAL AEROSOL CHEMILUMINESCENT DETECTION SYSTEM EMPLOYING THE SAME

BACKGROUND OF THE INVENTION (1) Field of the Invention

The present invention relates to a cyclone aerosol sampler mated with a chemiluminescent (CL) reagent injector and a biological aerosol CL detection system employing said cyclone aerosol sampler mated with said CL reagent injector. The interior surfaces of the cyclone aerosol sampler and the CL reagent injector employed are fabricated from materials that are free of metals that would initiate a CL-based reaction therein. The cyclone aerosol sampler employed serves as an aerosol sample collector as well as a CL reagent/sample mixing chamber. CL reagent is injected/introduced directly into the cyclone aerosol sampler during operation. Use of the sampler in a biological aerosol CL detection system provides a biological aerosol CL detection system having optimal sensitivity to the detection of biological materials in an aerosol sample. A method for detecting the presence of biological materials using the improved CL detection system herein is described.

(2) Description of the Related Art

Chemiluminescence (CL) has been used in the prior art for the detection and/or quantitative measurement of biological materials present in various types of samples. A CL technique taught by the prior art employs the use of a CL reagent such as luminol (5-amino-2,3-dihydro-1,4-phthalazinedione) in the presence of an oxygen donor reactant, such as hydrogen peroxide, which upon contact with biological materials produces detectable light via chemiluminescence. In operation, a collected sample is treated with a CL reagent that reacts with generic biological components present in the sample to produce detectable photons of light. These generic biological components initiate the CL-based reaction.

The principle of the luminol CL method for detecting bacteria is based on the following, well known, chemical reaction:

$$\text{Luminol} + H_2O_2 \xrightarrow{\text{hemin}} \text{aminopthalate} + N_2 + \text{light} \quad (1)$$

This CL reaction is proportional to the amount of biological material present in a test sample and is a sensitive means to identify biological material-containing samples. The luminol-based reaction is catalyzed by iron-containing macromolecules, such as hemins, which are ubiquitous to a wide variety of biological cells. Hemins include chemical materials, such as, Cytochrome C, microperoxidase, hemoglobins and the like. This chemical reaction, as set forth, serves as a means to rapidly detect and monitor the presence of and the amounts of materials of biological origin—i.e., those containing bacterial porphyrins.

Many CL detection systems are set forth in the prior art—Witz et al., U.S. Pat. No. 3,690,837; Witz et al., U.S. Pat. No. 3,754,868; Witz et al., U.S. Pat. No. 3,797,999; Soli, U.S. Pat. No. 3,567,586; Schiff et al., U.S. Pat. No. 4,765,961; Jeffers et al., U.S. Pat. No. 4,176,007; Chappelle et al., U.S. Pat. No. 4,385,113; and numerous others.

The use of a cyclone sampler for bioaerosols is taught in the prior art by Upton et al., "A Wind Tunnel Evaluation of the Physical Sampling Efficiencies of 3 Bioaerosol Samplers," *J. Aerosol Sci.*, Vol. 25, No. 8, pp 1493–1501 (1994). Upton et al. teach a cyclone sampler, Aerojet General Glass Cyclone, for the collection of biological samples, where the biological samples are collected in solution. The sample solution collected via the cyclone sampler is presumably later subjected to treatment with an assay.

The use of a cyclone sampler in a cellular material detection apparatus is taught by Squirrell in U.S. Pat. No. 5,773,710 and U.S. Pat. No. 5,918,259. In the Squirrell patents, a particulate fraction from a gaseous environment (sample) is collected in a processing fluid via the use of a cyclone sampler. The collected sample solution is then later treated with a luminescent reagent downstream from the cyclone sampler in the apparatus. The material from which the cyclone sampler is fabricated is not identified.

The invention herein provides a detection system employing a cyclone aerosol sampler having inner surfaces fabricated from specific materials, wherein the aerosol sample collected therein is collected in a dried state; it is not collected in solution prior to it being subjected to a CL reagent. The dry aerosol sample is directly mixed with a CL reagent within the cyclone aerosol sampler. The invention provides for a detection system having increased sensitivity and an optimum signal-to-noise ratio.

There exists a continuing need to provide improved apparatus and methods for the detection of the presence of biological materials in various samples employing the well known CL assay system described. Specifically, it would be desirable to provide an apparatus for detecting the presence of biological materials in aerosol samples, wherein the apparatus has high sensitivity to the presence of biological materials. It is further desirable to provide a detection system having minimal baseline CL signals, and hence enhanced sensitivity. The present invention describes such a system, wherein the system provides a simple and accurate means for detecting the presence of biological agents in an aerosol sample.

BRIEF SUMMARY OF THE INVENTION

The present invention relates to a cyclone aerosol sampler mated with a CL reagent injector and a biological aerosol chemiluminescent (CL) detection system employing said cyclone aerosol sampler mated with said injector, and a method for using the same in detecting the presence of biological materials in an aerosol sample. The CL reagent injector is mated with the cyclone aerosol sampler so as to deliver CL reagent directly to a collected aerosol sample therein. The cyclone aerosol sampler and the CL reagent injector employed are both fabricated from materials that are free of metals that would initiate a CL-based reaction with a CL reagent to be employed therein. The interior surface of the sampler and the interior surface of the CL reagent injector that are within the CL reagent path, in particular, must be composed of these materials.

Reference made herein to CL reagent path refers to and includes any and all surfaces that may come into direct contact with a CL reagent. For example, it includes the inner surfaces of any and all component parts of a CL detection system that come into contact with a CL reagent during system operation up to and including the luminometer measurement chamber. This would include, for instance, the inner surfaces of (1) a CL reagent injector (which includes a CL reagent reservoir and a CL reagent delivery means), (2) any injector tubing and connections, (3) a CL reagent input port, (4) a cyclone aerosol sampler, and (5) a catch tube or tubing path to a luminometer.

In order to provide a biological aerosol CL detection system, as described above, having optimal sensitivity to biological materials in an aerosol sample, the inventors determined that the CL reagent path employed must be free from metals that would initiate a CL-based reaction; or, stated differently, the CL reagent path must be free of metals that would initiate a reaction with a CL reagent to be employed therein, such as a luminol-containing CL reagent. Accordingly, the inner surfaces of the cyclone aerosol sampler employed and the inner surfaces of the CL reagent injector employed that are within the CL reagent path must be free from these types of metals. To optimize the sensitivity of a detection system within the scope of the present invention, it is critical that all parts of the detection system coming into direct contact with a CL reagent, up to and including the luminometer reading chamber, be composed/fabricated of materials that are free of these types of metals.

It is an object of the invention to provide a cyclone aerosol sampler mated with a CL reagent injector, wherein the inner surfaces of these are fabricated from materials that are free of metals that would initiate a CL-based reaction therein so as to provide a CL reagent path free of said metals.

It is an object of the present invention to provide a biological aerosol CL detection system having optimal sensitivity.

Still a further object of the present invention is to provide an improved biological aerosol CL detection system that provides a simple and accurate means for determining the presence of biological agents in a sample.

Yet a further object of the present invention is to provide a biological aerosol CL detection system employing a cyclone aerosol sampler mated with a CL reagent injector, wherein the inner surface of the cyclone aerosol sampler and the inner surface of the CL reagent injector employed are fabricated from materials that are free of metals that would initiate a CL-based reaction therein so as to provide a CL reagent path free from these metal.

It is an object of the present invention to provide a biological aerosol CL detection system having optimum sensitivity, wherein the entire CL reagent path stream therein is free from metals that would initiate a CL-based reaction.

Still a further object of the present invention is to provide a method for determining the suitability of a material for use throughout the CL reagent path of a biological aerosol CL detection system.

The means to achieve these and other objectives of the present invention will be apparent from the following description of the invention and claims.

BRIEF DESCRIPTION OF THE DRAWINGS

The present invention will be described with reference to the figures.

FIG. 6 illustrates the actual photon signal measured over time—background signal compared to 75,000 particles of Bg.

DETAILED DESCRIPTION OF THE INVENTION

Figure 1:
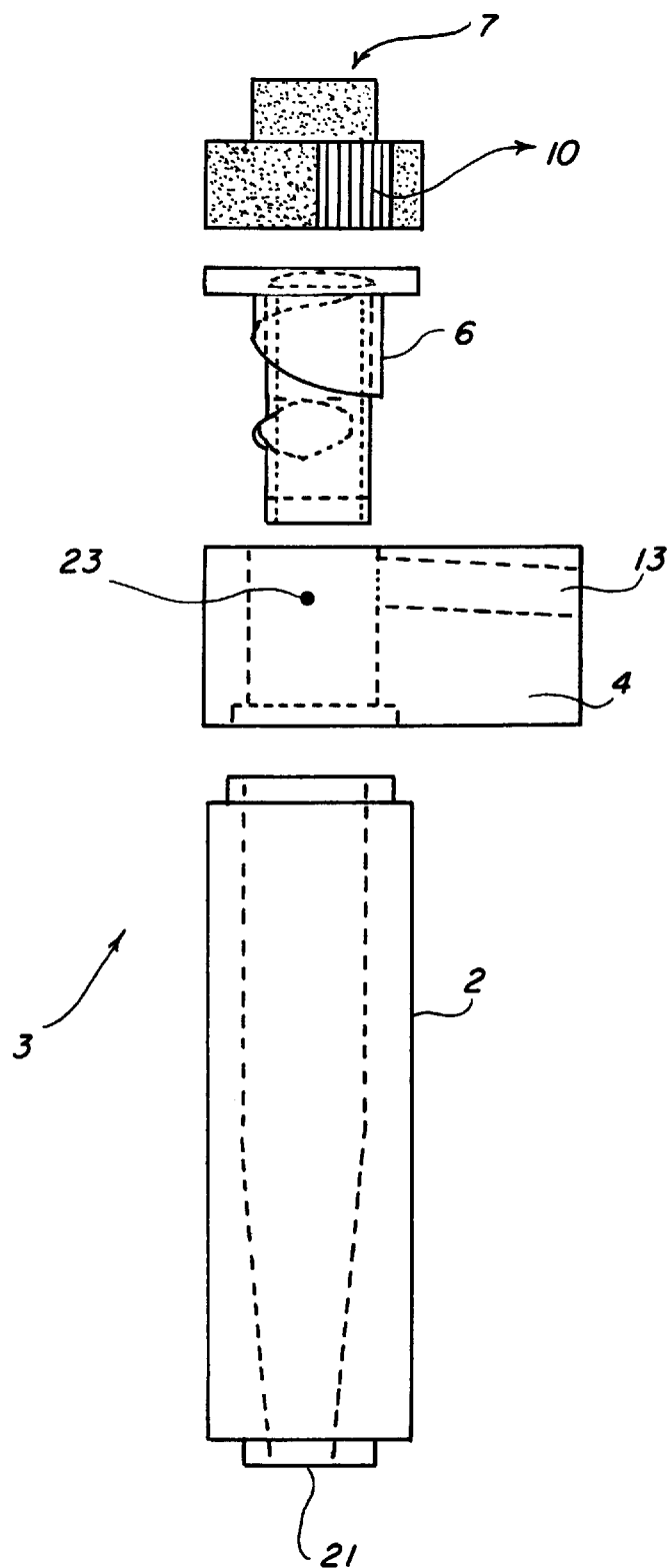
FIG. 1 illustrates a cyclone aerosol sampler of the type that may be employed within the scope of the present invention.

The present invention relates to an improved biological aerosol CL detection system having optimal sensitivity to the detection of the presence of biological materials in an aerosol sample. The system is a low-cost, discriminating biological aerosol CL detector for the rapid and sensitive detection or monitor of aerosols of biological origin. The biological aerosol detection system herein may be either automated or manually operated.

The biological aerosol CL detection system of the present invention comprises a cyclone aerosol sampler mated with a CL reagent injector, and a luminometer. The inner surface of the cyclone aerosol sampler and the inner surface of the CL reagent injector are composed of materials that are free of metals that would initiate a CL-based reaction with a CL reagent to be employed therein—i.e., a luminol-based CL reagent, so as to provide a CL reagent path free of these metals. The combination of a cyclone aerosol sampler mated with a CL reagent injector, wherein the inner surfaces of both are fabricated from these materials is novel and claimed herein.

The CL reagent injector is mated with the cyclone aerosol sampler so as to be in a position to introduce/inject a CL reagent directly therein. In the biological aerosol CL detection system herein and the method employing it, CL reagent is introduced or injected directly into the sampler wherein an aerosol sample has been collected. The cyclone aerosol sampler serves to facilitate the collection of an aerosol sample to be evaluated for the presence of biological materials and also serves to facilitate the mixing of the collected aerosol sample and the CL reagent supplied thereto by the CL reagent injector. It serves as an aerosol sample collector as well as a CL reaction chamber.

The importance of using specific materials, and consequently avoiding others, within the CL reagent path of the detection system herein was determined by the inventors. They found that detectable photons of light are produced by the exposure of standard CL reagents to surfaces fabricated from or containing certain metals. (See, i.e., Surface Material Testing below.) These metals are said to initiate a CL reaction. The inventors refer to these types of metals as metals that initiate a CL-based reaction or metals that initiate a CL reaction with a CL reagent employed. Because the detection system of the present invention uses CL as the means to detect the presence of biological materials in a sample, it was determined that the presence of metals in the CL reagent path therein that would initiate CL during use would effect the sensitivity and accuracy of the apparatus. In summary, the inventors have determined that the type of materials present in the component parts of a system within the CL reagent path stream therein effects the actual sensitivity performance of the biological aerosol CL detection system.

The inventors have discovered that in order to provide a biological aerosol CL detection system having optimum sensitivity, all parts of the detection system coming into direct contact with a CL reagent during operation, up to and including the luminometer reading chamber, must be free from metals that would initiate a CL-based reaction therein. Accordingly, the interior surfaces of the cyclone aerosol sampler employed within the scope of the present invention and the interior surfaces of the CL reagent injector employed herein, where these interior surfaces are within the CL reagent path, must be fabricated from materials that are free of these types of metals. It is critical that these surfaces be free of metals that would initiate a reaction with a CL reagent to be employed.

The inventors found that the type of materials present in the CL reagent path of a sampler, for instance, can contribute to the baseline (also referred to herein as background) CL signal generated by the CL detection system. Baseline CL signals generated by the exposure of a standard luminol CL reagent to surface metals, such as stainless steel (Note Surface Material Testing described below), iron and nickel, for instance, were found to be significant. Baseline CL signal is defined as the signal generated by a CL detection system from the evaluation of a standard CL reagent having no sample present therein. It is desirable to eliminate or keep baseline-CL signal to a minimum so as to provide a detection system having optimal signal-to-noise ratio. The biological aerosol CL detection system within the scope of the present invention minimizes or eliminates the presence of baseline CL signal by using throughout its CL reagent path (i.e., as the interior surfaces of the cyclone aerosol sampler and the CL reagent injector) materials that are free of metals that would initiate a CL-based reaction therein, and hence contribute to baseline CL-signal. The entire CL reagent path within the scope of the present invention is free of these metals.

In the CL detection system within the scope of the present invention, it is critical that the entire path of the biological aerosol CL detection system that comes into contact with the CL reagent, up to and including the luminometer reading chamber, be fabricated from materials that are free of metals that would initiate a CL-based reaction therein.

Materials suitable for use throughout the entire CL reagent path of the detection system herein may, in general, be any material from which the component parts of the invention within the CL reagent path may be physically fabricated, using conventional means, provided that these materials are free of metals that would initiate a CL-based reaction with the specific CL reagent to be employed within the CL reagent path. For example, copper, iron, nickel and stainless steel were found to initiate a luminol-based CL reaction of the type set forth in equation (1). Materials suitable for use in the CL reagent path of a detection system employing a luminol-based CL reagent are to be free of these metals so as to provide a detection system having optimum sensitivity. The presence of these and other metals having like CL-initiating properties in the CL reagent path of a CL detection system in which a luminol-based CL reagent is to be employed would contribute to the baseline CL-signal of the aerosol detection system, and therefore reduce its sensitivity. Maximum sensitivity of the CL detection system is obtained when the presence of these types of metals are avoided.

Determination of the types of metals to avoid in the CL path of a CL detection system can be determined by exposing a specific metal contemplated for use within a CL reagent path to the CL reagent to be used therein, and then collecting the exposed CL reagent and evaluating the exposed CL reagent for the production of detectable photons of light using a photon counter. This measurement is then compared to a measurement obtained using a control surface material, such as glass. If the detected photon emissions measured for the CL reagent exposed to the metal surface is statistically greater than that observed for the CL reagent exposed to the control surface material, use of the specific metal is to be avoided in the CL reagent path of a CL detection system wherein the specific CL reagent tested is to be employed. This method can further be used to confirm the suitability of a material to employ as well.

Based on the above description, one having ordinary skill in the art would be able to determine the types of metals to avoid in the CL path of biological aerosol CL detection systems employing specific CL reagents. Moreover, based on this description, the skilled artisan will be able to select suitable materials to employ throughout the CL reagent path of a detection system within the scope of the present invention.

Plastics and glass were determined to be suitable materials for use herein throughout the entire CL reagent path of the biological aerosol detection system within the scope of the present invention. Plastics with chemical resistance to high pH solutions of approximately 9–13 and plastics that can be sterilized by either chemical, thermal or radiation means in the event of contamination are preferred. Preferred plastics also have chemical resistance to moderate alcohol concentrations ranging from approximately 10–20% v/v. Plastics that might crack, soften or dissolve in alcohols (i.e., ethanol) are to be avoided. Suitable plastics having these preferred characteristics include polypropylene, polystyrene, polyvinylidene fluoride (PVDF), modified polyphenelyene oxide (PPO) and Ultem® (General Electric) polyetherimide and the like. Commercial grades of these types of plastics may be employed.

Although plastics and glass are identified as suitable materials to employ throughout the entire CL reagent path of the biological aerosol detection system herein, one having ordinary skill in the art, based on the description of the present invention, will be able to select other suitable materials to employ as well. Moreover, one having ordinary skill in the art will recognize that the materials used throughout the CL reagent path need not be limited to one suitable material. For instance, the inner surface of the cyclone aerosol sampler may be composed of one suitable material (i.e., plastic A) and the inner surface of the CL reagent injector may be composed of a different suitable material (i.e., plastic B or even glass).

Without wishing to be bound by theory, if, for example, a metal sampler were used wherein the metal is one that would initiate a CL-based reaction, it is presumed that the high pH of the CL (luminol) reagent (pH of approximately 13) coming into contact with the metal therein would act to remove sufficient metal ions from the sampler so as to initiate the CL-based reaction and, therefore, produce detectable light.

As already described, the biological detection system herein employs a cyclone aerosol sampler mated with a CL reagent injector. A cyclone aerosol sampler within the scope of the present invention generally comprises a cyclone body, one or more inlet ports through which an aerosol sample can be directed or drawn and a CL reagent introduced, and a fan. Means to facilitate the mixing of a sample with a CL reagent may be present therein. A cyclone aerosol sampler of the type that may be employed herein can be more specifically described with reference to FIG. 1. Sampler 3 comprises primarily four component parts: cyclone body 2, sample intake housing (also referred to as aerosol intake housing) 4, mixer insert 6 and fan assembly 7. Sample intake housing 4 comprises aerosol sample intake port 13 into which aerosol samples for evaluation are either directed or drawn, and CL reagent input port 23. Mixer 6 is a hollow sleeve with an external rifling or ridge and serves as the inner sleeve of the sampler assembly 3. Mixer 6 is attached to fan assembly 7, and slides into the sample intake housing 4 as illustrated. Mixer insert 6, is one of three custom fabricated components of the sampler 3. (Fan assembly 7 is commercially available.) These custom fabricated components may all be fabricated from materials, such as plastics, or other materials that are free of metals that would initiate a CL-based reaction with a CL reagent to be employed therein. The cyclone aerosol sampler 3 is mated with a CL reagent injector 5 (not shown) in a fashion illustrated in FIG. 2. When in use, a test sample enters the sampler 3 via aerosol sample intake port 13 and is treated with a CL reagent via CL reagent input port 23. The sampler 3 has treated sample exit port 21 through which treated samples exit and are collected using, for example, a catch tube 9 (not shown—see FIG. 2). The inner surfaces of all of the component parts of sampler 3 that may come into contact with the CL reagent are fabricated from materials that are free of metals that would initiate a reaction with a CL reagent to be employed. Note that although the sampler 3 may be entirely fabricated from these materials, it need not be. As already described above, what is critical is that the inner surfaces of the sampler 3, the portion of the sampler that comes into direct contact with the CL reagent, be fabricated from specific materials so as to provide a CL reagent path free of the presence of metals that would initiate a CL-based reaction. How sampler 3 is employed in the biological aerosol detection system within the scope of the present invention is set forth in FIG. 2.

Figure 2:
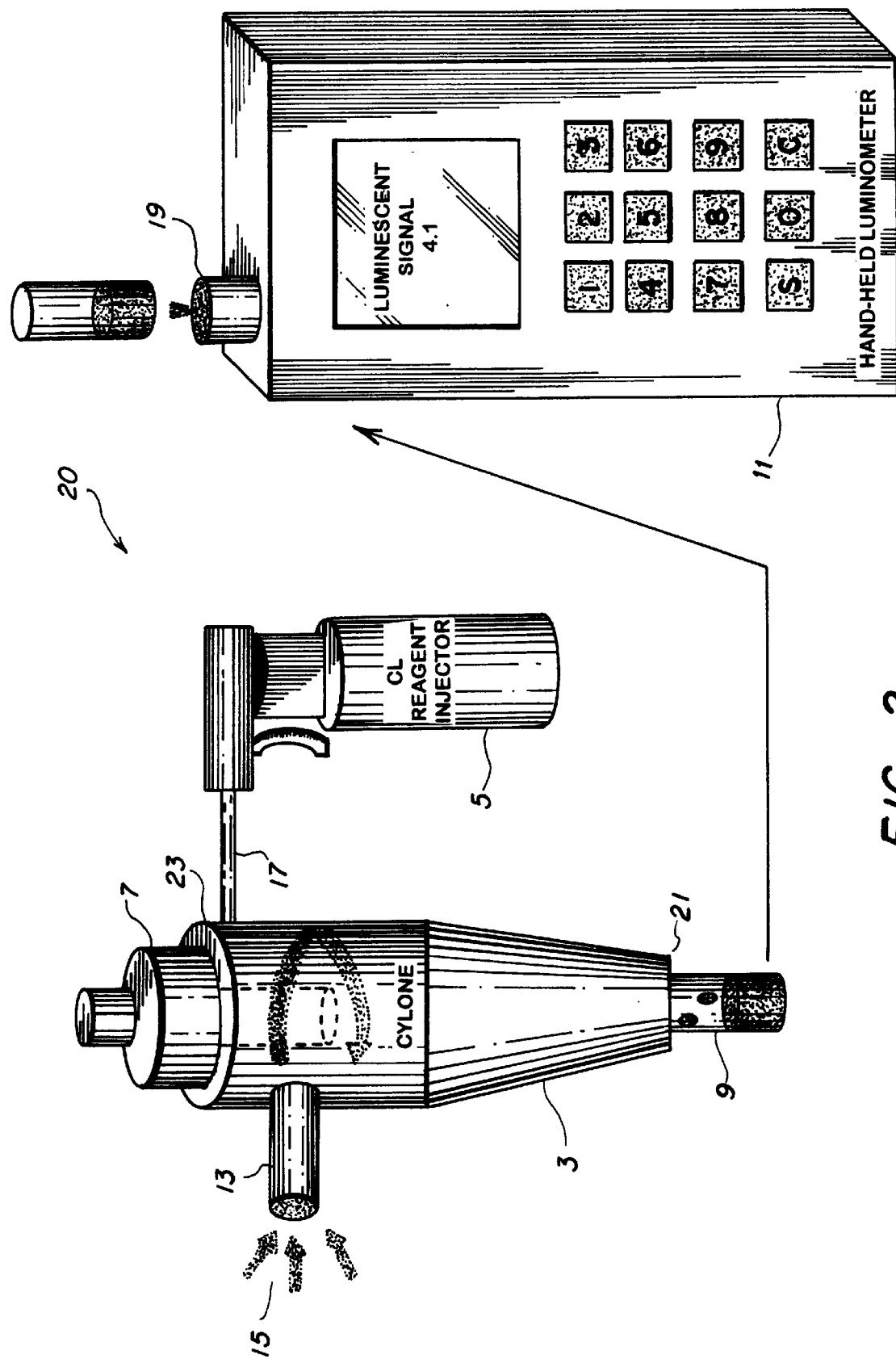
FIG. 2 illustrates a schematic view of a biological aerosol CL detection system within the scope of the present invention.

FIG. 2 illustrates a biological aerosol detection system 20 of the type within the scope of the present invention. The detection system 20 comprises primarily cyclone aerosol sampler 3, chemiluminescent (CL) reagent injector 5, catch tube 9 and luminometer 11. The cyclone aerosol sampler 3 has CL reagent input port 23 to which CL reagent injector 5 is connected via connecting tubing or channel 17 which is connected to the injector mechanism. CL reagent injector 5 may be connected, or mated, with sampler 3 via CL reagent input port 23 in any conventional fashion. Cyclone aerosol sampler 3 further comprises aerosol sample intake port 13, through which aerosol sample 15 is collected for evaluation and testing. Fan 7 is positioned in cyclone aerosol sampler 3 so as to draw sample 15 into the aerosol sampler 3. Fan 7 provides the vacuum pressure to draw aerosol sample 15 into the intake port 13. Cyclone aerosol sampler 3 also has mixer insert 6 (not shown) which forces inlet aerosol samples 15 to spin in a cyclone fashion within the sampler 3. The mixer 6 is hollow so as to permit the air to exit the sampler body via the fan exhaust port 10 (not shown, see FIG. 1).

Except for the cyclone aerosol sampler 3, the biological aerosol detection system 20 may be assembled from commercially available component parts.

The cyclone aerosol sampler may be molded or machined in any fashion well within the skill of the art using, for example, the types of plastics previously set forth. Polypropylene and polystyrene may be, for example, used in molding the cyclone aerosol sampler herein; while PVDF, PPO and Ultem® polyetherimide may be used for machining the sampler. Samplers 3 have been machine fabricated in a conventional fashion from Kynar® (PVDF manufactured by Atochem) and Noryl® (PPO manufactured by GE Plastics). These particular plastics were selected based on their properties relating to machinability, chemical resistivity and ability to be sterilized after exposure to biologicals. Plastics having like properties may be employed herein as well.

Fans such as those manufactured by Micronel (#U64HM-6V) may be employed in the cyclone aerosol sampler described. Any fan or other means that would serve the purpose of drawing a sample into the sampler and helping to facilitate the mixing of the aerosol sample and CL reagent within the cyclone aerosol sampler may be used herein. The fan employed may be operated by various power sources, such as, for example purpose only, a 12 volt battery or 120 V electrical current. The DC fan operates in the 6–12 volt range depending upon air flow desired. Optimal voltage settings are 8–9 volts. One having ordinary skill in the art and understanding the purpose for which the fan is employed will be able to select a suitable fan or other means to be employed herein.

CL reagent injectors, as used herein, refer to apparatus of the manual or automated type that include a reagent reservoir as well as a reagent delivery means. Only those apparatus having inner surfaces that are composed of materials that are free of metals that would initiate a CL-based reaction with the CL reagent to be placed therein may be employed in the present invention. To be employed within the scope of the invention, all inner surfaces of a CL reagent injector that are within the CL reagent path must be free from metals that would initiate a CL-based reaction. These types of apparatus are commercially available. A manual CL reagent injector is one that an operator could use to intermittently inject a predetermined amount of CL reagent into the cyclone aerosol sampler. For example, a Jet-Pipet Repetitive Dispensor (#H-07999-03), manufactured by Cole Parmer, may be used as the manual CL reagent injector herein. The Jet-Pipet Repetitive Dispensor is capable of 1 milliliter reagent injection. The manual CL reagent injector described could be substituted with a powered injection system either custom assembled or available commercially. Commercially available pumps such as syringe infusion pumps (i.e., those manufactured by Tri-Continent, Harvard Apparatus, ISCO, Inc.) or simple peristaltic pumps (such as those manufactured by Cole-Palmer, Winston-Marlow) could serve as CL reagent injectors in this system. One having ordinary skill in the art will recognize that any means for supplying and introducing a CL reagent into the cyclone aerosol sampler for the purposes described and in the fashion described may be employed as the CL reagent injector herein.

CL reagents that may be employed in the present invention are those that upon their coming into contact with biological materials in an aerosol sample, CL is produced for detection by a luminometer. Luminol is the substrate in the CL reagent employed in the evaluation of the present invention. A suitable CL reagent mixture or solution may comprise luminol, an oxygen donor (such as hydrogen peroxide), a chelator for trace metal ions (such as ethylene diamine-tetra-acetic acid (EDTA)), ethanol and an alkaline salt (such as potassium hydroxide). The alkaline salt serves to raise the pH of the reagent. A CL reagent of the type that may be employed within the scope of the present invention comprises 20–600 mL luminol, 0.0015–0.006% w/v hydrogen peroxide, approximately 10 mM EDTA (optional) and 10% v/v ethanol. The standard CL reagent solution comprises 136 $\mu$M luminol, 10 mM potassium hydroxide, 16.2 mM EDTA (di-sodium salt) 1.8 M ethanol, 66.7 mM urea and 0.006% w/v hydrogen peroxide. Optimal sensitivity is obtained when the concentration of luminol and hydrogen peroxide in this standard CL reagent solution is changed to 20 $\mu$M and 0.002% (w/v) respectively. A commercial grade of luminol (i.e., Aldrich #12,307-2) may be employed as the substrate in the CL reagent herein; or a commercial grade of luminol may be purified in well known conventional fashions, such as by alkaline recrystallization and then employed as the substrate in the CL reagent. Studies performed indicate that improvements in net signal are obtained with the use of recrystallized luminol reagent.

Conventional, commercially available benchtop luminometers (i.e., EG&G, Turner Designs, GEM Biomedical)

or hand-held luminometers (i.e., IDEXX and Randox) may be used in the detection system. An integrating luminometer with an optical sensitivity range over at least 7 log units is preferred. Moreover, it is preferable that the luminometer employed be portable so as to allow for system portability. As an alternative, these luminometers could be adapted for flow through readings so that a reagent/sample mixture could be measured immediately as it exits the cyclone sampler. Technology exists so that one having ordinary skill in the art could readily design and assemble such a joint cyclone sample collection and detection system having flow through capabilities for use herein.

Catch tubes of the type that may be employed herein are essentially test tube-like receptacles fabricated from materials such as plastics or glass so as to permit the CL measurement of a sample mixture therein to be made using a luminometer. Catch tubes of this sort are commercially available. As an alternative, the catch tube employed might be substituted with a flow tube for directing the CL mixture from the cyclone sampler to a luminometer, for instance, adapted for flow through readings. One having ordinary skill in the art will be able to identify catch tubes and flow tubes that may be employed within the scope of the invention.

In operation, aerosol sample 15 and CL reagent are caused to enter cyclone aerosol sampler 3 at aerosol sample intake port 13 and CL reagent input port 23, respectively. The aerosolized particles 15 are drawn into the sampler inlet 13 by fan 7 over a fixed time period (i.e. 1–5 minutes) where they fall into the lower end of the cyclone sampler 3. The collected aerosol sample 15 is mixed with the CL reagent injected by CL reagent injector 5 through CL reagent inlet port 23. In addition to drawing in aerosol sample 15, fan 7 helps facilitate the mixing of the sample 15 and CL reagent once in the sampler 3. The resultant mixture of the sample and CL reagent exits sampler 3 via treated sample exit port 21 and drips into catch tube 9, which is immediately transported in a conventional fashion to luminometer sampler port 19 of a hand held luminometer 11 for measurement of any generated light signal. After a 12-second signal-integration period, the results are displayed on the LCD screen of the luminometer 11 as a log value of the integrated photon count.

In an alternative embodiment, the CL reagent/sample mixture could be delivered directly into a flow cell within a modified luminometer for measurement (not shown). Thus eliminating the step of transporting tube 9' to luminometer sampler port 19.

The system described could be converted into a fully automated injection and analysis system by someone skilled in the art. For instance, an automated, powered CL reagent injection system may be employed and a flow through feature may be incorporated into the luminometer reader. Laboratory luminometers can be adapted for flow through readings.

The biological aerosol CL detection system of the present invention provides a low cost, easily portable detector or trigger for biological aerosols that may be present in most environments. It also provides a simple and accurate means for determining the presence of biological agents in a sample. Except for the cyclone aerosol sampler employed herein, off-the-shelf, commercially available components may be employed for the other component parts of the biological aerosol CL detection system described.

The present invention may be further described by way of example. These examples are in no way to be construed as limiting the scope of the invention.

Surface Material Testing

Tests were performed to determine the effect that the exposure of a standard CL reagent to various clean surfaces has on the generation of background CL signal. Specifically, tests were performed to estimate the degree of metal ion contamination (which contributes to interference) present from the brief exposure of a standard CL reagent to (1) a porcelain crucible, (2) a stainless steel spatula, and (3) an aluminum weighing dish. A borosilicate glass surface served as the control surface since original sensitivity testing was performed in glass cuvettes.

The standard CL reagent employed in this test comprises 136 $\mu$M luminol, 10 $\mu$M potassium hydroxide, 16.2 mM EDTA (di-sodium salt), 1.8 M ethanol, 66.7 mM urea and 0.006% (w/v) hydrogen peroxide.

Figure 3:
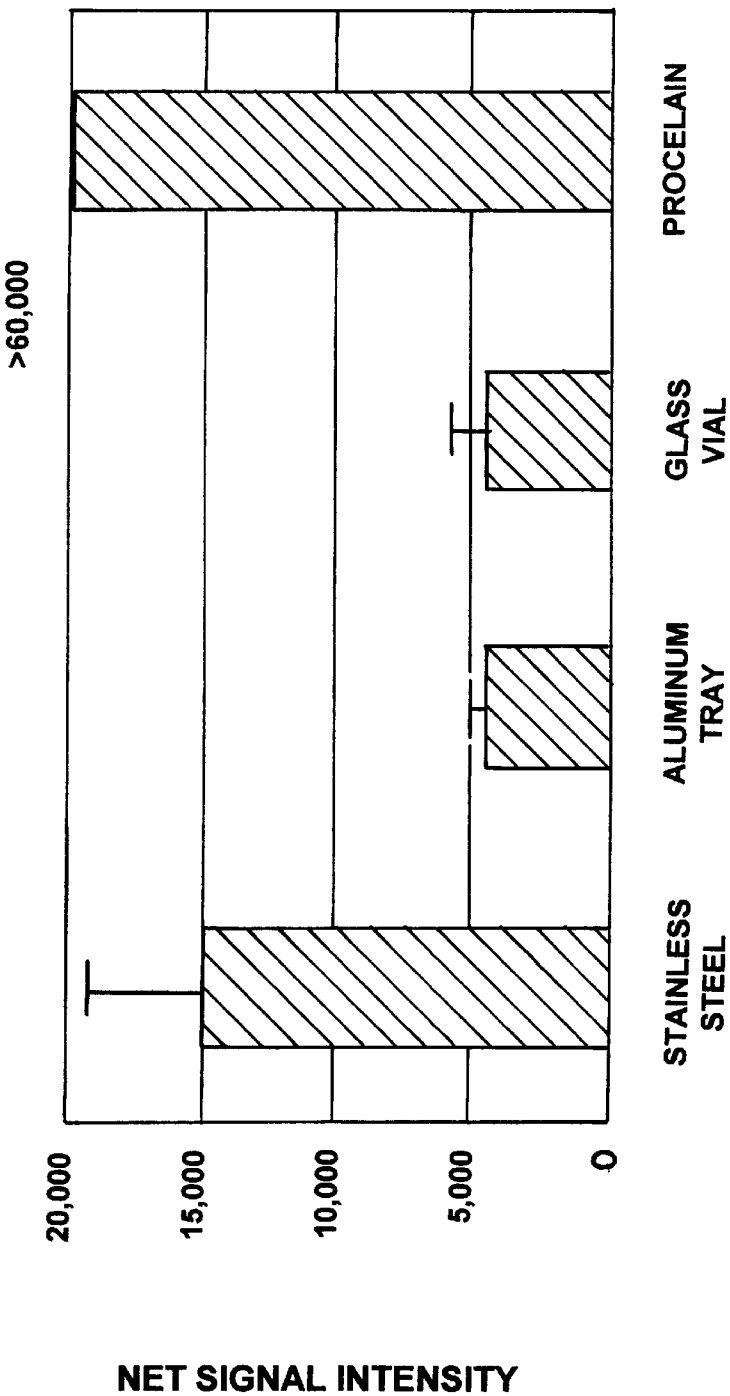
FIG. 3 illustrates the net signal intensity of a standard CL reagent (1/10 dilution) when exposed to various clean surfaces

100 $\mu$l of the standard CL reagent was placed onto the various surfaces for a period of 10 seconds. The reagent was then recovered and added to 900 $\mu$l of fresh (unexposed) reagent for luminescence measurement. Measurements were made using a Packard Scintillation Counter set to photon counting mode. Trials were repeated three times and the results set forth in FIG. 3.

Note that the porcelain crucible gave the highest background signal, followed by the stainless steel spatula. The inventors concluded that even after only a ten second exposure of one-tenth of a reagent (only 1/10 of test sample was exposed to test surfaces), background CL signals for stainless steel and porcelain were significant. High background signals result in decreased sensitivity. This test illustrates the criticality in selecting specific materials to be employed, and those to be avoided, within the CL reagent path stream of a biological detection system to provide a detection system having optimal sensitivity.

EXAMPLE I

A manually operated biological aerosol detection system as set forth in FIG. 2 was assembled. The sampler 3 employed was machined from Noryl®. A high efficiency fan blower (Micronel #U64HM-6V) 7, a Jet-Pipet Repetitive Dispensor (Cole Parmer #H-07999-03) 5 for the injection of 1 milliliter of CL reagent, a 10×75 mm borosilicate glass catch tube 9 to receive the reagent after injection and an IDEXX Lightning Luminometer 11 for signal measurement were used. The DC fan employed was powered between 6–9V either directly from a direct current power source or battery, or through a power converter connected to 120 V wall power.

Air sampling velocity is adjustable and can be optimized for particle collection efficiency following subsequent planned controlled aerosol chamber tests. The fan selected, which facilitates the air sampling velocity, has the capability of pulling up to 320 liters of air per minute in an open system. The fan, when set to 90 liters/minute in the sampler system herein, is expected to draw approximately 400 mA at 6 volts power. A one pound nickel-cadmium rechargeable battery pack can be employed herein. This battery can provide sufficient power for at least 8 hours of continuous sampling time. As an alternative, a 2.3 pound military specification 15 volt alkaline disposable pack (SAFT #BA-5590/U) may be used. It is able to provide sufficient power for at least 40 hours of continuous sampling time.

As a preliminary test of the system, rooftop testing of the manually operated system was conducted to (1) determine the environmental background conditions and signals (at ambient conditions), and (2) to evaluate performance to challenges with unknown concentrations of Bg simulant.

To determine the environmental (ambient) background conditions and signals, the sampler was run continuously for up to an hour at approximately 90 liters/minute. One milliliter of a standard CL reagent (600 $\mu$M luminol; 0.006% hydrogen peroxide; 10 mM EDTA; 10% ethanol, titrated with potassium hydroxide until pH 13) was injected into the sampler every two minutes; and light output from the resulting sample was read in the IDEXX luminometer. These output readings represent the baseline reading.

After multiple exposures to ambient conditions had been recorded, a 50 ml tube containing dried Bg spores was opened and agitated gently for 10 seconds. This was performed directly in front of the sample intake port of the sampler during a standard two-minute sampling period.

Figure 4:
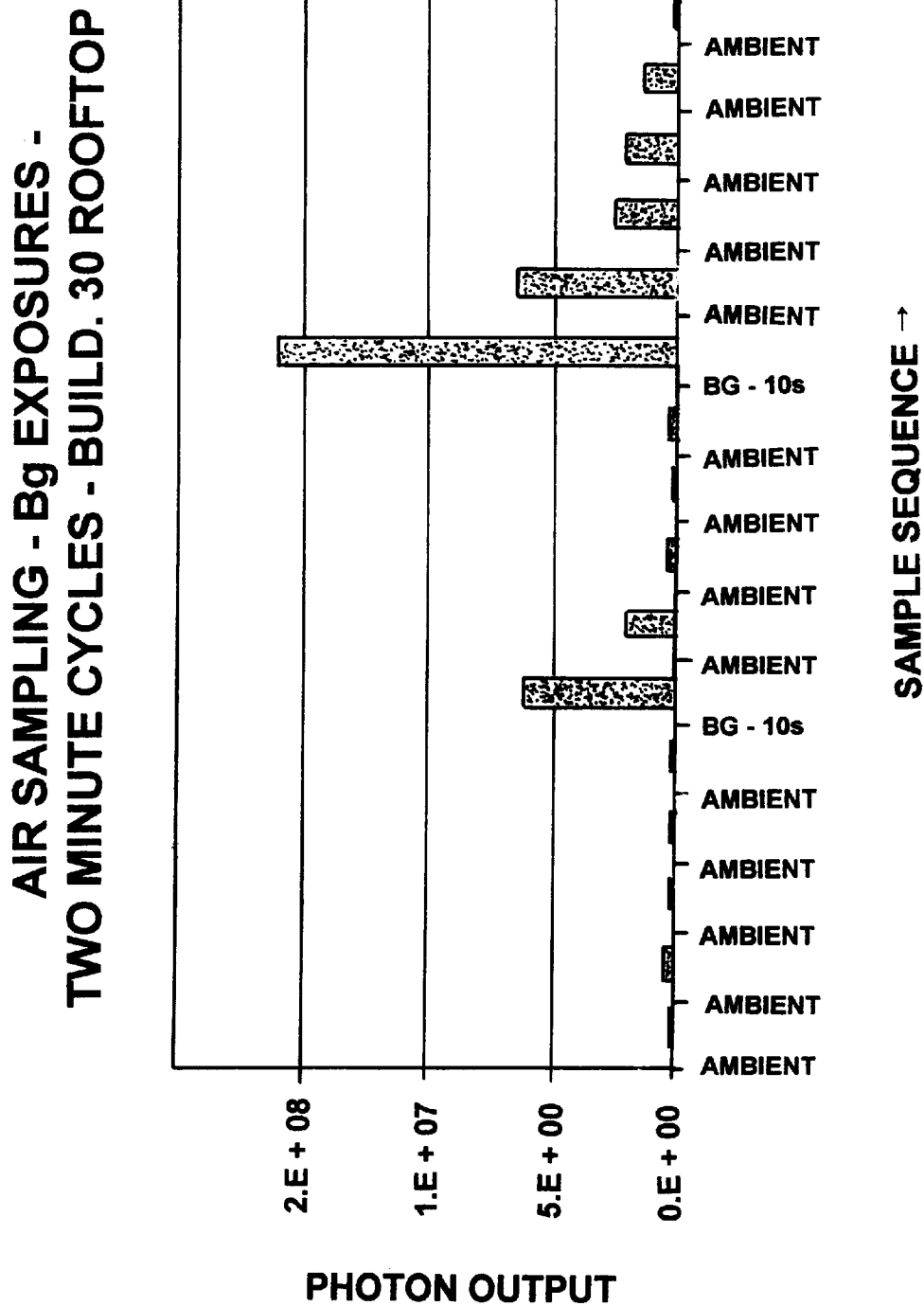
FIG. 4 illustrates the photon output for air sampling and Bg (*Bacillus Globigii*) spore exposures at 2 minute cycles.

The CL reagent was then injected as during the ambient readings and the resulting sample/CL reagent mixture evaluated in the luminometer. FIG. 4 summarizes the test sequence of these results. Note that the background readings are minimal as compared to when the Bg sample was introduced. This indicates a strong signal-to-noise ratio. Moreover, note that two Bg exposures resulted in immediate increases in photon output over background noise shown (40-fold and 80-fold, respectively). Also significant is the observation that these large increases in signal (presumably due to Bg spores in the sampler) returned to background levels within 2 cycles in the first challenge and 5 cycles in the second challenge. These preliminary tests indicate that:

(1) samples containing Bg spores are in fact collected by the plastic sampler;
(2) the manually operated biological aerosol CL system can and does detect these collected spores; and
(3) high levels of Bg spores do not cause significant contamination or carry-over from one test sample to the next.

The last observation is especially significant because plastic samplers have often been avoided in aerosol collection applications because of the concern that biological components would adhere strongly to walls of plastic samplers. These preliminary results serve to alleviate this concern.

EXAMPLE II

Figure 5:
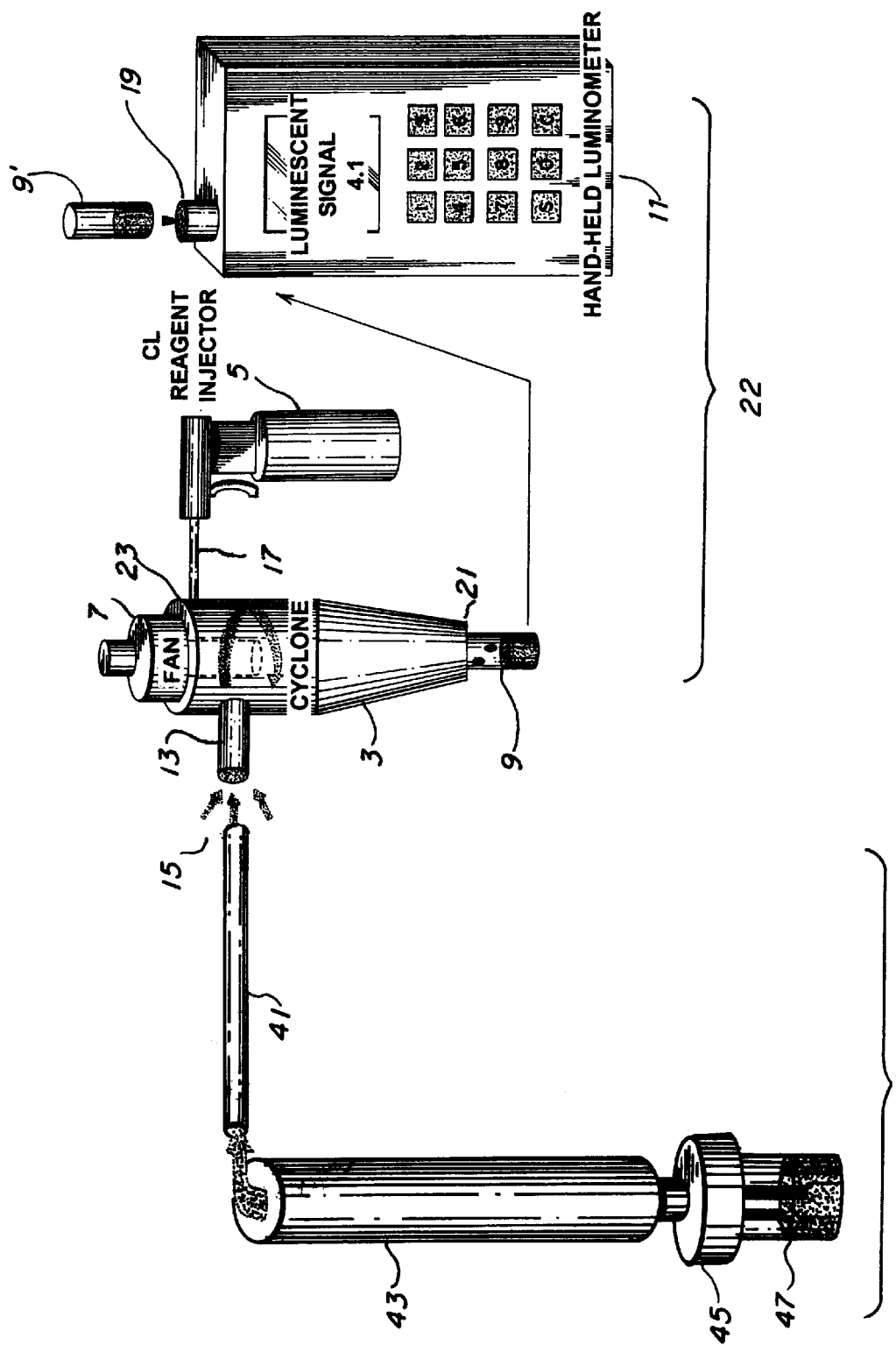
FIG. 5 sets forth a biological aerosol nebulizer system used for evaluating a biological aerosol detection system within the scope of the present invention.

In order to further evaluate the overall performance of the manual chemiluminescent detector system set forth in Example I, controlled chamber tests with known aerosol concentrations of biological simulants were conducted. Reference is made to FIG. 5 to describe the methodology employed.

A known quantity of bacteria was delivered directly into the sampler over a fixed period of time using a nebulizer apparatus 48 comprising Colison nebulizer (BGI Incorporated) 45, bacterial suspension container (BGI Incorporated) 47, drying chamber 43 and tubing extension 41. Air sampling velocity, which is adjustable, was set at approximately 90 liters/minute. The biological aerosol detection system 22, was placed in a chemical fume hood during the sampling process in order to minimize the potential for environmental background interference.

Overnight bacterial suspensions of Bg grown in standard nutrient broth and diluted with distilled water (typically, at ratios of 1:1 and up to 1:4) (in container 47) were aerosolized in Colison nebulizer 45 and dried in glass chamber 43 with pressurized nitrogen gas before being delivered into the cyclone sampler 3 through a tubing extension 41. The nebulizer 48 was set to deliver approximately 75,000 particles of Bg per minute. The bacteria concentration exiting the nebulizer apparatus through tubing extension 41 over a fixed period of time was determined using a TSI Aerosol Particle Sizer (not shown). The nebulizer apparatus 48 was then directed into the cyclone aerosol sampler 3 to presumably deliver thereto the same number of bacterial particles as that determined by the TSI Aerosol Particle Sizer over a fixed period of time.

One ml of CL reagent was injected into sampler 3 via CL reagent input port 23 by CL reagent injector 5 every minute. The CL reagent employed contained 20$\mu$minol and 0.002% hydrogen peroxide. The CL reagent was collected at the bottom of the sampler 3, via treated sample exit port 21, and into catch tube 9, and read immediately in the luminometer 11 (Lightning Luminometer).

FIG. 6 illustrates the actual photon output as measured by the luminometer 11 during consecutive one-minute cycles. As can be seen from this Figure, Bg aerosol was delivered twice within a series of background collections under a chemical fume hood. At both of these times, one sees that a three-fold increase of signal over background interference was measured. Similar results were observed when a sampler machined from Kynar® was used in place of the Noryl® sampler.

When Bg particles were delivered at a lower concentration of approximately 30,000 particles per minute, signal-to-noise ratio was found to be approximately 2 to 1. These results illustrate that the use of the plastic sampler herein mated with a CL reagent injector in a biological aerosol detection system within the scope of the present invention provides a biological aerosol detection system having superb sensitivity to Bg particles.

The present invention has significant application in both domestic and international markets where monitoring of biological agents is useful. For example purposes only, the detection system herein could find use in transportation hubs, municipal buildings, sports venues, government facilities, etc.

One skilled in the art will note that the present invention provides a biological aerosol CL detection system having high sensitivity to biological agents. The system herein is low cost and requires low power sources for operation. A significant advantage of the present system is that, aside from the cyclone sampler, it can be assembled from mostly commercially available components. In addition, the present invention provides for a system that can be portable and is inexpensive to operate and maintain. Moreover, the present invention may be employed in most environments.

The biological aerosol CL detection system herein could serve readily as a front-end triggering alarm for biological agent identifying technologies already in production within the biodefense community. Analytical technologies that provide identification or confirmation of a specific type of biological agent, such as with antibody-based or molecular-probe assays, are both costly and time-consuming. A generic biological detector, such as described herein, would indicate or signal that a given air sample contained a biological agent and should be tested by these more rigorous methods. Thus, the present invention could serve as a screening device to eliminate probable negative samples from having to be subjected to these subsequent analyses steps.

While particular embodiments of the present invention have been shown and described, it will be obvious to those skilled in the art that changes and modifications may be made without departing from this invention. Therefore, it is intended that the claims herein are to include all such obvious changes and modifications as fall within the true spirit and scope of this invention.

We claim:

1. A combined aerosol sampler and chemiluminescent reagent/aerosol sample mixing chamber apparatus comprising
   a cyclone aerosol sampler; and
   a means for introducing a chemiluminescent reagent into said cyclone aerosol sampler;
   wherein said means for introducing said chemiluminescent reagent into said cyclone aerosol sampler contains a chemiluminescent reagent therein and is positioned adjacent to said cyclone aerosol sampler so as to be in a position to introduce said chemiluminescent reagent into said cyclone aerosol sampler; and
   wherein said inner surface of said cyclone aerosol sampler and the inner surface of said means for introducing a chemiluminescent reagent into said cyclone aerosol sampler are composed of materials that are free of metals that would initiate a chemiluminescent reaction with said chemiluminescent reagent.

2. The apparatus of claim 1, wherein said materials that are free of metals that would initiate a chemiluminescent reaction with said chemiluminescent reagent are plastics.

3. The apparatus of claim 2, wherein said plastics are plastics with chemical resistance to pH of approximately 9–13.

4. The apparatus of claim 2, wherein said plastics are selected from the group consisting of polypropylene, polystyrene, polyvinylidene fluoride, modified polyphenelyene oxide and Ultem polyetherimide.

5. The apparatus of claim 1, wherein said materials that are free of metals that would initiate a chemiluminescent reaction with said chemiluminescent reagent is glass.

6. The apparatus of claim 1, wherein said cyclone aerosol sampler comprises an aerosol sample intake port and a chemiluminescent reagent input port.

7. The apparatus of claim 1, wherein said means for introducing a chemiluminescent reagent into said cyclone aerosol sampler is a chemiluminescent reagent injector.

8. The apparatus of claim 7, wherein said chemiluminescent reagent injector is an intermittent chemiluminescent reagent injector.

9. The apparatus of claim 1, wherein said chemiluminescent reagent comprises luminol.

10. A biological aerosol chemiluminescent detection system comprising
    a cyclone aerosol sampler;
    a means for introducing a chemiluminescent reagent into said cyclone aerosol sampler; and
    a luminometer,
    wherein said means for introducing a chemiluminescent reagent into said cyclone aerosol sampler contains a chemiluminescent reagent therein and is positioned adjacent to said cyclone aerosol sampler so as to be in a position to introduce said chemiluminescent reagent into said cyclone aerosol sampler; and
    wherein said inner surface of said cyclone aerosol sampler and the inner surface of said means for introducing a chemiluminescent reagent into said cyclone aerosol sampler are composed of materials that are free of metals that would initiate a chemiluminescent reaction with said chemiluminescent reagent.

11. The biological aerosol chemiluminescent detection system of claim 10, wherein said materials that are free of metals that would initiate a chemiluminescent reaction with said chemiluminescent reagent are plastics.

12. The biological aerosol chemiluminescent detection system of claim 11, wherein said plastics are plastics with chemical resistance to pH of approximately 9–13.

13. The biological aerosol chemiluminescent detection system of claim 11, wherein said plastics are selected from the group consisting of polypropylene, polystyrene, polyvinylidene fluoride, modified polyphenelyene oxide and Ultem polyetherimide.

14. The biological aerosol chemiluminescent detection system of claim 10, wherein said materials that are free of metals that would initiate a chemiluminescent reaction with said chemiluminescent reagent is glass.

15. The biological aerosol chemiluminescent detection system of claim 10, wherein said cyclone aerosol sampler comprises an aerosol sample intake port and a chemiluminescent reagent intake port.

16. The biological aerosol chemiluminescent detection system of claim 10, wherein said means for introducing a chemiluminescent reagent into said cyclone aerosol sampler is a chemiluminescent reagent injector.

17. The biological aerosol chemiluminescent detection system of claim 16, wherein said chemiluminescent reagent injector is an intermittent chemiluminescent reagent injector.

18. The biological aerosol chemiluminescent detection system of claim 10, wherein said chemiluminescent reagent comprises luminol.

19. The biological aerosol chemiluminescent detection system of claim 10, wherein said biological aerosol chemiluminescent detection system further comprises a catch tube positioned beneath said cyclone aerosol sampler.

20. A chemiluminescent method for detecting the presence of biological materials in an aerosol sample, said method comprising
    providing a cyclone aerosol sampler;
    drawing or directing an aerosol sample to be evaluated into said cyclone aerosol sampler;
    introducing into said cyclone aerosol sampler containing said aerosol sample a chemiluminescent reagent in an amount sufficient to generate a chemiluminescent reaction in the presence of biological materials that may be present in said aerosol sample;
    permitting said aerosol sample and said added chemiluminescent reagent to be mixed within said cyclone aerosol sampler;
    collecting said mixture of said aerosol sample and said chemiluminescent reagent exiting from said cyclone aerosol sampler; and
    measuring any emitted light of said mixture of said aerosol sample and said chemiluminescent reagent using a luminometer so as to determine the presence of biological materials therein,
    wherein the inner surface of said cyclone aerosol sampler is composed of material that is free of metals that would initiate a chemiluminescent reaction with said chemiluminescent reagent.

21. The method of claim 20, wherein said chemiluminescent reagent is introduced intermittently into said cyclone aerosol sampler containing said aerosol sample.

22. The method of claim 20, wherein said cyclone aerosol sampler comprises an aerosol sample intake port and a chemiluminescent reagent intake port.

23. The method of claim 20, wherein said material that is free of metals that would initiate a chemiluminescent reaction with said chemiluminescent reagent is a plastic.

24. The method of claim 23, wherein said plastic is a plastic with chemical resistance to pH of approximately 9–13.

25. The method of claim 23, wherein said plastic is selected from the group consisting of polypropylene, polystyrene, polyvinylidene fluoride, modified polyphenelyene oxide, and Ultem polyetherimide.

26. The method of claim 20, wherein said material that is free of metals that would initiate a chemiluminescent reaction with said chemiluminescent reagent is glass.

27. The method of claim 20, wherein said chemiluminescent reagent comprises luminol.

28. A method for determining the suitability of a material for use in a chemiluminescent reagent path of a biological aerosol chemiluminescent detection system, wherein said method comprises selecting a material to be tested for its suitability for use in a chemiluminescent reagent path of a biological aerosol chemiluminescent detection system;

selecting a chemiluminescent reagent to be used in said biological aerosol chemiluminescent detection system;

exposing said material to said chemiluminescent reagent;

collecting said chemiluminescent reagent after its exposure to said material;

measuring the presence of any emitted light from said collected chemiluminescent reagent after its exposure to said material; and comparing said measurement to a measurement obtained using a control surface material.

29. The method of claim 28, wherein said chemiluminescent reagent comprises luminol.

30. The method of claim 28, wherein said material is exposed to said chemiluminescent reagent for approximately 10 seconds.

31. The method of claim 28, wherein the presence of any emitted light from said collected chemiluminescent reagent is measured using a photon counter.

32. The method of claim 28, wherein said control surface material is glass.

* * * * *